United States Patent [19]

Bridges

[11] Patent Number: Plant 7,737

[45] Date of Patent: Dec. 10, 1991

[54] LINVILLE MINIATURE ROSE

[76] Inventor: Dennis A. Bridges, 2734 Toney Rd., Lawndale, N.C. 28090

[21] Appl. No.: 584,335

[22] Filed: Sep. 17, 1990

[51] Int. Cl.[5] ..... A01H 5/00

[52] U.S. Cl. ..... Plt./8

[58] Field of Search ..... Plt. 8

*Primary Examiner*—James R. Feyrer

[57] ABSTRACT

A new and distinct variety of miniature rose plant characterized by a profusion of blooms that are near white with a soft pink center. The exhibition form blooms are held on long stems on a very strong upright plant.

1 Drawing Sheet

BACKGROUND OF THE INVENTION

1. Field of the Invention

The present invention relates to a new and distinct variety of miniature rose plant which has been given the international variety recognition designation "Brilin", and is to be marketed in this country under the synonym "Linville".

2. Plants Related to the Invention

The plant of this invention was originated as a result of a planned breeding program which had as a seed parent an unnamed seedling which is unpatented and proprietary and which had, itself, resulted from the cross of my unnamed proprietary seedling with the commercial variety "Rise'N Shine", as pollen parent. Flowers of the seed parent of the plant of this application were variously pollinated with pollen from a number of sources. Seeds resulting from such crosses were massed, and caused to germinate. Plants resulting were allowed to develop and the progeny were observed in hope of attaining at least one valuable addition to roses of this market class by expressing desired traits which had not been previously seen. The plant of this application was one of the progeny of such efforts.

SUMMARY OF THE INVENTION

Among the new and novel characteristics which are possessed by this plant, singly and in combination, which distinguish it from its parents and all other plants of which I am aware are:

1. Well formed, off-white and blemish resistant blooms with a soft, pink center and exceptional form and substance.
2. Abundant blooms borne singly, and it clusters of up to 7, on long, strong stems.
3. A light, spicy fragrance.
4. An abundance of semi-glossy, medium green foliage which pleasingly contrasts with and highlights the blooms of soft creamy hues.
5. Higher than usual disease resistance to common rose diseases, with a higher than usual level of vigor, and growing to a height which is unusual for roses of this market class to produce a plant which attractively appoints the home garden while providing cut flowers of exhibition form and quality.

BRIEF DESCRIPTION OF THE DRAWING

The single sheet of the accompanying drawing is a photograph which shows typical specimens of the flowers of the new variety in different stages of development as well as the coloration thereof as accurately as possible in color illustrations of this type.

BOTANICAL DESCRIPTION

The following is a detailed botanical description of my new variety of miniature rose, with color terminology in accordance with The Royal Horticultural Society Colour Chart (RHSCC), except where common dictionary terms of color definition are employed.

Type: Hardydwarf, bushy, compact, seedling, greenhouse, outdoors, cut flower, garden decoration, potted plant.
Commercial class: Miniature.
International recognition name: "Brilin".
Commercial synonym: "Linville".

FLOWER

Observations were made from specimens grown outdoors at Cleveland County, N.C., U.S.A., in June 1990.

Type: Miniature rose.
Blooming habit: Continuous.
Bud:
- *Size.*—Large—Mature bud just before opening $1\frac{1}{2}$ cm in length.
- *Form.*—Pear shaped.
- *Color.*—When sepals first divide. — Near white (19-D). When petals begin to unfurl. — Inside: Pale pink (49-D). Outside: Near white (19-D). When half-blown. — Inside: Pale pink (49-D) with outer petal being near white (19-D). Reverse side of petals being near white (19-D).

Sepals: As long as the bud, thin, pointed, serrated with several appendages (0.7 cm in length).
- *Peduncle.*—$1\frac{1}{2}$ inches in length, erect, green.

Bloom:
- *Size.*—2 inches when fully expanded.
- *Borne.*—Singly and in clusters of up to 5 blooms.
- *Form.*—High centered blooms reflex gently and hold that high center.
- Petalage.—32.
- *Color.*—During first two days: Inner petals at center of flower: Pale pink (49-D). Outer petals: Near white (19-D). Base of petals (point of attachment): Near white (19-D). Reverse of petals: Near white (19-D). General tonality from a distance: Near white (19-D) with a very pale pink center (49-D).

Color change:

*As bloom ages.*—Near white (19-D).
*General tonality.*—Near white (19-D).
*After three or more days.*—Near white (19-D).

Petals:
*Texture.*—Thick — With good substance.
*Appearance.*—Velvety.
*Form.*—Oval, curling gently as bloom opens.
*Arrangement.*—Regular.
*Petaloids in center.*—Few.
*Persistence.*—Petals drop off cleanly.
*Fragrance.*—Slightly spicy.
*Lasting quality.*—Flowers last several days on the plant or as a cut flower.

REPRODUCTIVE ORGANS

Stamens, filaments and anthers:
*Arrangement.*—Irregularly arranged around styles.
*Color.*—Yellow.

Pollen: Golden yellow.

Styles: Uneven length, thin loosely arranged.

Stigmas:
*Color.*—Green.

Hips:
*Shape.*—Globular.
*Size.*—½ in diameter.
*Color.*—Light green.
*Seeds.*—Seeds do not protrude.

Plant

Form: Upright.

Growth: Very vigorous, slight outward uniform branching, with approximately 10 main canes producing numerous flower stems. 30 to 36 inches in height upon maturity.

Foliage:
*Size.*—Medium for a miniature — Each leaf in a leaflet is 2½ to 3 cm in length.
*Quantity.*—Abundant.

*Color.*—New foliage: Upper side: Glossy dark green near to B137 with red veins. Under side: Slightly lighter green, red veins. Old foliage: Upper side: Dark green near to B138. Under side: Slightly lighter green.
*Shape.*—Oval and pointed.
*Texture.*—Upper side: Thick slick. Under side: Smooth.
*Edge.*—Serrated.
*Serration.*—Regular.
*Leaf stem.*—Color: Dark green.
*Stipules.*—½ inch long, then.
*Disease resistance.*—Blackspot; good; mildew, good; rust, good.

Wood:
*New wood.*—Green near to A143. Bark: Smooth.
*Old wood.*—Medium green near to C141. Bark: Smooth.

Thorns:
*Quantity.*—Few.
*Form.*—Straight, sharp, with oval base.
*Length.*—⅜ inches in length.
*Color when young.*—Near to A174 at base. Near to B 174 at tip.
*Position.*—Irregular.

Prickles:
*Quantity.*—None.

Winter hardiness: Very hardy with little die back.

I claim:

1. A new and distinct variety of rose plant of the miniature rose class, substantially as herein shown and described, characterized particularly by an abundance of exhibition quality near white blooms with centers of soft pink, unusually strong substance, firm thick petals, borne singly and in sprays, on a tall plant with semi-glossy dark green foliage, said plant being easy to propagate from cuttings, and said blooms being long lasting both on the plant and as cut flowers.

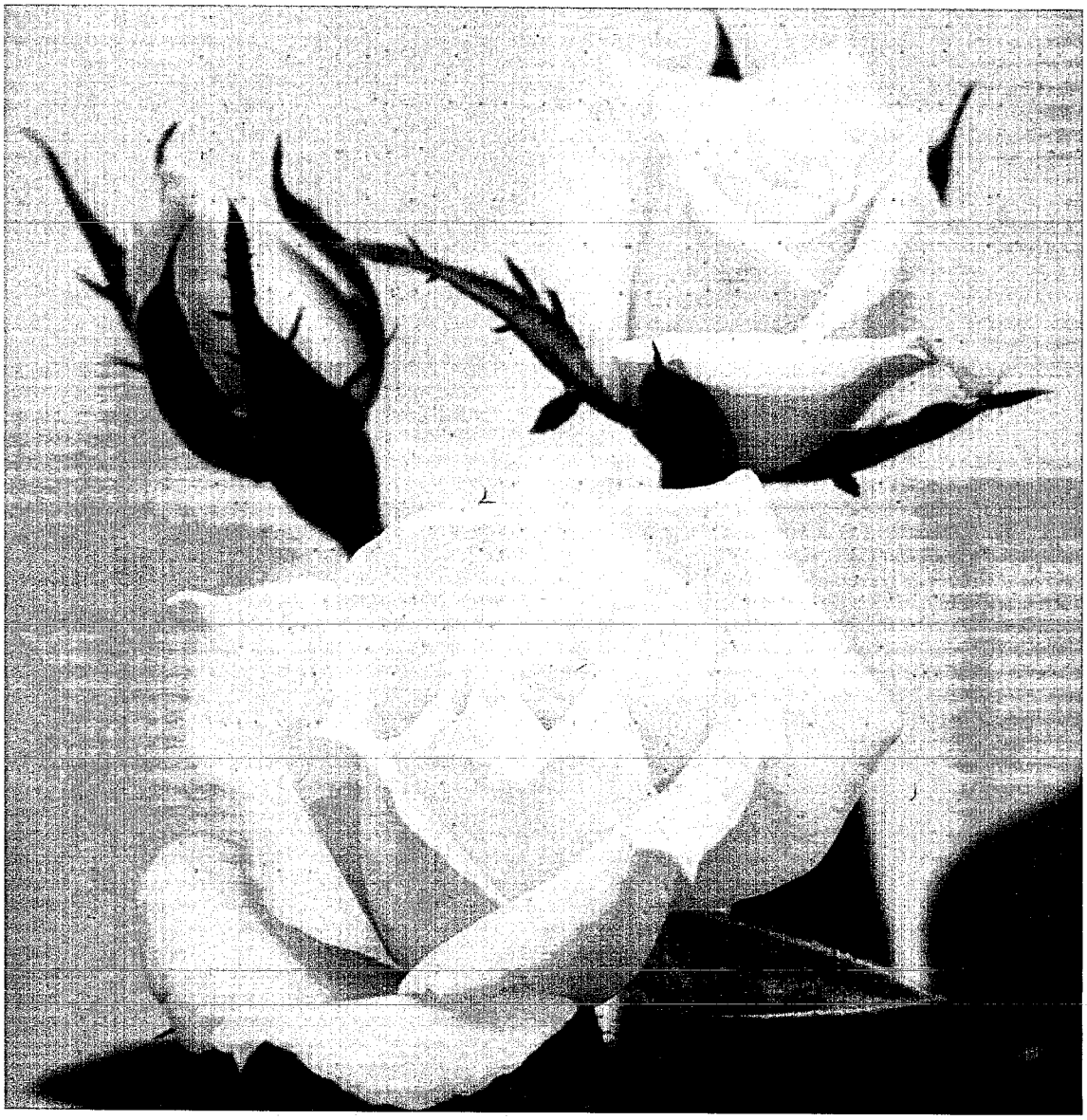

* * * * *